United States Patent
Motil et al.

(10) Patent No.: US 11,219,612 B2
(45) Date of Patent: Jan. 11, 2022

(54) NUTRACEUTICAL FORMULATION FOR UNBLOCKING RECEPTORS

(71) Applicant: DREMCUBED, LLC, North Olmsted, OH (US)

(72) Inventors: Amy Motil, North Olmsted, OH (US); Matt Motil, North Olmsted, OH (US)

(73) Assignee: DREMCUBED, LLC, North Olmsted, OH (US)

( * ) Notice: Subject to any disclaimer, the term of this patent is extended or adjusted under 35 U.S.C. 154(b) by 0 days.

(21) Appl. No.: 16/897,475

(22) Filed: Jun. 10, 2020

(65) Prior Publication Data

US 2020/0390734 A1    Dec. 17, 2020

Related U.S. Application Data

(60) Provisional application No. 62/859,897, filed on Jun. 11, 2019.

(51) Int. Cl.

| | |
|---|---|
| *A61K 36/28* | (2006.01) |
| *A61K 31/202* | (2006.01) |
| *A61K 9/00* | (2006.01) |
| *A61K 31/352* | (2006.01) |
| *A23L 33/135* | (2016.01) |
| *A23L 33/105* | (2016.01) |
| *A61K 35/00* | (2006.01) |

(52) U.S. Cl.
CPC .......... *A61K 31/202* (2013.01); *A23L 33/105* (2016.08); *A23L 33/135* (2016.08); *A61K 9/0053* (2013.01); *A61K 31/352* (2013.01); *A61K 36/28* (2013.01); *A23Y 2220/03* (2013.01); *A23Y 2240/75* (2013.01); *A61K 2035/115* (2013.01)

(58) Field of Classification Search
None
See application file for complete search history.

(56) References Cited

U.S. PATENT DOCUMENTS

| | | |
|---|---|---|
| 6,358,521 B1 | 3/2002 | Izvekova et al. |
| 7,582,674 B2 | 9/2009 | Raederstorff et al. |
| 9,855,235 B2 | 1/2018 | Zemel et al. |
| 10,646,535 B1 | 5/2020 | Paul |
| 2003/0185911 A1 | 10/2003 | Qazi et al. |
| 2010/0173024 A1 | 7/2010 | McDaniel |
| 2011/0159121 A1 | 6/2011 | McDaniel |
| 2013/0261183 A1* | 10/2013 | Bhagat .............. A61P 35/00 514/560 |
| 2014/0107193 A1* | 4/2014 | Kuang .............. A23L 33/16 514/456 |
| 2015/0335577 A1 | 11/2015 | Agueros Bazo et al. |
| 2020/0078333 A1* | 3/2020 | Postrel ............ A61K 31/352 |
| 2021/0051987 A1* | 2/2021 | Shi .................. A23L 33/125 |

FOREIGN PATENT DOCUMENTS

WO    2013012760 A1    1/2013

OTHER PUBLICATIONS

McPartland, JM, et al. Care and Feeding of the Endocannabinoid System. PLoS ONE 9(3)1-36, Mar. 12, 2014. (Year: 2014).*
Russo, E. Beyond Cannabis: Plants and the Endocannabinoid System. Trends in Pharmacological Sciences 37(7)594-606 Jul. 2016. (Year: 2016).*
Cohen, J., The Bliss Gene: FAAH SNPs (rs324420), (https://selfhacked.com/blog/thebliss-gene-faah-snps-rs324420/ last accessed Mar. 20, 2019), Jan. 16, 2016.

* cited by examiner

*Primary Examiner* — Ralph J Gitomer
(74) *Attorney, Agent, or Firm* — Jacob M. Ward; Ward Law Office LLC

(57) ABSTRACT

A nutraceutical formulation used to unblock receptors is disclosed herein. The nutraceutical formulation used to therapeutically treat humans includes arachidonic acid, docosahexaenoic acid (DHA), *echinacea*, kaempferol, coffee fruit, and probiotics.

2 Claims, No Drawings

NUTRACEUTICAL FORMULATION FOR UNBLOCKING RECEPTORS

CROSS REFERENCE TO RELATED APPLICATIONS

This application claims the benefit of U.S. Provisional Application Ser. No. 62/859,897, filed on Jun. 11, 2019. The entire disclosure of the above application is hereby incorporated herein by reference.

FIELD

The present disclosure relates to nutraceuticals and, more particularly, to a nutraceutical formulation for use in unblocking endocannabinoid system receptors.

BACKGROUND

The endocannabinoid system (ECS) is a biological system composed of endocannabinoids, which are endogenous lipid-based retrograde neurotransmitters that bind to cannabinoid receptors, and cannabinoid receptor proteins that are expressed throughout the vertebrate central nervous system and peripheral nervous system.

The endocannabinoid system is involved in regulating a variety of physiological and cognitive processes including fertility, pregnancy, during pre- and postnatal development, appetite, pain-sensation, mood, and memory, and in mediating the pharmacological effects of *cannabis* and cannabidiol (CBD).

The ECS is also involved in mediating some of the physiological and cognitive effects of voluntary physical exercise in humans and other animals, such as contributing to exercise-induced euphoria as well as modulating locomotor activity and motivational salience for rewards. In humans, the plasma concentration of certain endocannabinoids (i.e., anandamide) have been found to rise during physical activity.

Two primary endocannabinoid receptors have been identified: CB1 and CB2. CB1 receptors are found predominantly in the brain and nervous system, as well as in peripheral organs and tissues, and are the main molecular target of the endocannabinoid ligand (binding molecule), anandamide, as well as its mimetic phytocannabinoid, THC.

One other main endocannabinoid is 2-arachidonoylglycerol (2-AG), which is active at both cannabinoid receptors, along with its own mimetic phytocannabinoid, CBD. 2-AG and CBD are involved in the regulation of appetite, immune system functions, and pain management.

As of 2020, forty-two states in the United States have legalized the use of marijuana in some form. Medical marijuana is growing in popularity to treat a wide variety of ailments. Unfortunately, as a patient repeatedly uses medical marijuana, the patient may begin to develop a tolerance. The patient will need to ingest larger amounts of marijuana to receive a therapeutic dose of cannabinoids.

Increase usage of marijuana over time may lead to adverse effects the patient may not have otherwise been susceptible to, for example, damage to the lungs caused by increased smoking of marijuana. Additionally, with an increased therapeutic dose, the patient is more likely to experience psychoactive effects from the marijuana. A patient may have to alter their medical marijuana regime in order to avoid such psychoactive effects where the patient has to work, for example.

The build-up of the patient's tolerance over time may be cause by blocked or saturated endocannabinoid receptors. Thus, it is desirable for the patient to be able to unblock these receptors, which may ultimately militate against the formation of a tolerance.

There is a continuing need for a nutraceutical formulation that contains ingredients that may unblock saturated receptors. Desirably, the nutraceutical formulation will permit continued use of cannabinoids without requiring increases in dosage to obtain similar effects.

SUMMARY

In concordance with the instant disclosure, a nutraceutical formulation that contains ingredients that may unblock receptors, and which will permit continued use of cannabinoids without requiring increases in dosage to obtain similar effects, has surprisingly been discovered.

Certain ingredients have been found useful for unblocking receptors when provided in appropriate concentrations. Nutraceutical supplements made from combinations of these ingredients are useful for supplying these ingredients in effective amounts, especially when unblocking receptors is desirable. The nutraceutical formulation according to the present disclosure is particularly useful for unblocking cannabinoid receptors.

It should be appreciated that the nutraceutical formulation of the present disclosure is also useful for increasing the efficacy at the unblocked receptors. The nutraceutical formulation may increase effectiveness for the desired compounds to bind to the cannabinoid receptors CB1 and CB2.

In an exemplary embodiment, the nutraceutical formulation includes arachidonic acid, docosahexaenoic acid (DHA), *echinacea*, kaempferol, and probiotics. Specifically, the arachidonic acid, DHA, *echinacea*, kaempferol, and probiotics, all function synergistically to unblock receptors. The formulation may be orally ingested in a variety of dosage forms, for example, as a capsule or tablet.

In another embodiment, the nutraceutical formulation may include arachidonic acid, DHA, *echinacea*, kaempferol, coffee fruit, probiotics, and at least one additional ingredient. The additional ingredient may be one of green tea-EGCG, chocolate, and an aromatic spice.

Further areas of applicability will become apparent from the description provided herein. It should be understood that the description and specific examples are intended for purposes of illustration only and are not intended to limit the scope of the present disclosure.

DETAILED DESCRIPTION

The present invention is directed to a nutraceutical formulation, containing arachidonic acid, docosahexaenoic acid (DHA), *echinacea*, kaempferol, coffee fruit, and at least one probiotic.

The terminology used in the specification provided herein below is hereby defined to include similar and/or equivalent terms, and/or alternative embodiments that would be considered obvious to one skilled in the art given the teachings of the present patent application. Additionally, the words "a," "an," and "one" are defined to include one or more of the referenced items unless specifically stated otherwise. Also, the terms "have," "include," "contain," and similar terms are defined to mean "comprising" unless specifically stated otherwise.

Except where otherwise expressly indicated, all numerical quantities in this description are to be understood as modified by the word "about" in describing the broadest scope of the technology. When describing weight percentages of various ingredients in formulations of the present disclosure, as set forth hereinbelow, the term ""about" is hereby defined to mean within plus or minus five weight percent (±5 wt %) by weight relative to a total weight of the formulation. Additionally, when describing weight percentages of the various ingredients, it should be appreciated that these percentages are relative to the total weight of the formulation less a weight of the at least probiotic present in the formulation.

The present disclosure is directed to a nutraceutical formulation. The nutraceutical formulation may include arachidonic acid, docosahexaenoic acid, *echinacea*, kaempferol, and at least one probiotic. Each of these ingredients may be powdered or granulated prior to being incorporated into the nutraceutical formulation.

For example, the natural ingredients may be powdered or granulated to a particle size between about 10 microns and about 300 microns, and more particularly between about 100 microns and about 200 microns. However, one of ordinary skill in the art may select other suitable particle sizes, including particle sizes adapted to facilitate water solubility of the nutraceutical formulation as described further herein below, as desired. Furthermore, each of these natural ingredients may be substantially evenly mixed together according to conventional techniques to provide the nutraceutical formulation for convenient end use, as described further herein.

In particular examples, the ingredients are provided in a dosage form suitable for oral administration, including one or more tablets or artificial capsules, a manufactured or compounded liquid or slurry form, or as a manufactured powder or granulate.

As a nonlimiting example, the powder or granulate form of the nutraceutical formulation may be water soluble. In particular, the nutraceutical formulation may be ground to, or otherwise provided in, a particle size that is adapted to naturally dissipate and dissolve within an aqueous medium. It should be appreciated that where the powdered or granulated ingredients of the nutraceutical formulation are dehydrated, the ingredients will furthermore more readily absorb water and dissolve in the aqueous medium, especially in comparison to synthetic vitamin alternatives. One of ordinary skill in the art may also select other suitable dosage forms within the scope of the present disclosure.

It should be appreciated that the capsule dosage form for the nutraceutical formulation may be preferred. Where provided in a capsule dosage form, the artificial capsules may be single-piece or two-piece manufactured bodies for encapsulation of the formulation. As further non-limiting examples, suitable ingredients for the manufactured capsules may include wax, cellulose (including, for example, Hypromellose or HPMC, and sometimes referred to as "veggie capsule"), starches, gelatin, pullulan/tapioca, and combinations thereof. Other suitable ingredients for capsules of the present disclosure may also be employed, as desired.

Other ingredients can be included, such as various excipients, including one or more antiadherents, binders, coatings, disintegrants, flavors, colors, lubricants, glidants, sorbents, preservatives, and sweeteners. Excipient examples include one or more of hypromellose, rice flour, magnesium stearate, cellulose, inulin, and silicon dioxide. One of ordinary skill in the art may also select other suitable dosage forms and capsule types within the scope of the present disclosure.

Arachidonic acid has been found useful for the unblocking of receptors. Arachidonic acid is a polyunsaturated omega-6 fatty acid. Arachidonic acid is present in red meat, eggs, algae, and fish oil. Arachidonic acid may also be produced by the fungus *Mortierella alpine*. The arachidonic acid from *Mortierella alpine* may be highly purified before use in the present nutraceutical formulation.

More specifically, arachidonic acid has been found to interact with cannabinoid receptors. Namely, arachidonic acid has been found to bind to the CB1 cannabinoid receptor.

The arachidonic acid may be present in a concentration ranging from about 10 to about 70 weight percent, more particularly about 30 percent to about 60 percent, and most particularly about 53 percent, each by weight relative to the total weight of the nutraceutical formulation less a weight of the at least one probiotic. A skilled artisan may also select other suitable concentrations for the arachidonic acid component, as desired.

In particular, where the nutraceutical formulation is provided in a 17,400 mg daily dose, the arachidonic acid may be present in an amount of approximately 1,500 mg to 10,500 mg, more particularly approximately 4,500 mg to 9,000 mg, and most particularly about 8,000 mg. A skilled artisan may select any suitable amount of arachidonic acid for each particular daily dose of the nutraceutical formulation, as desired.

Docosahexaenoic acid (DHA) has been found useful for unblocking receptors. DHA is an omega-3 fatty acid that is a primary structural component of the human brain, cerebral cortex, skin, and retina. DHA can be synthesized from alpha-linolenic acid or obtained directly from maternal milk (breast milk), fish oil, or algae oil. In certain embodiments, the DHA may be 80% DHA source from algae.

More specifically, DHA is believed to have a positive effect on the endocannabinoid system. In the endocannabinoid system, DHA may allow for the production of certain molecules that benefit brain activity. DHA has further been found to reduce downstream endocannabinoid and inflammatory gene expression.

The DHA may be present in a concentration ranging from about 5 to about 40 weight percent, more particularly about 15 percent to about 30 percent, and most particularly about 19 percent. A skilled artisan may also select other suitable concentrations for DHA component, as desired.

In particular, where the nutraceutical formulation is provided in a 17,400 mg daily dose, the DHA may be present in an amount of approximately 750 mg to 6,000 mg, more particularly approximately 2,250 mg to 4,500 mg, and most particularly about 3,300 mg. A skilled artisan may select any suitable amount of DHA for each particular daily dose of the nutraceutical formulation, as desired.

*Echinacea* has been found useful for the unblocking of receptors. *Echinacea* is a genus of herbaceous flowering plants in the daisy family. Three species from the *Echinacea* genus may be used for therapeutic uses, namely, *Echinacea purpurea*, *Echinacea angustifolia*, and *Echinacea pallida*. *Echinacea purpurea* root powder may be cultivated from dried and ground roots of the plant. One such powder is available from Starwest Botanicals, Inc., which is located in Sacramento, Calif.

*Echinacea* may be present in a concentration ranging from about 1 to about 10 weight percent, more particularly about 1 percent to about 5 percent, and most particularly about 2 percent. A skilled artisan may also select other suitable concentrations for *Echinacea* component, as desired.

In particular, where the nutraceutical formulation is provided in a 17,400 mg daily dose, the *Echinacea* may be present in an amount of approximately 150 mg to 1,500 mg, more particularly approximately 150 mg to 750 mg, and most particularly about 400 mg. A skilled artisan may select any suitable amount of *Echinacea* for each particular daily dose of the nutraceutical formulation, as desired.

Kaempferol has been found useful for the unblocking of receptors. Kaempferol is a natural flavanol, which is a type of flavonoid. Flavanols may be found in a variety of plants and plant-derived foods including kale, beans, tea, spinach and broccoli. Kaempferol may be bio-synthesized from phenylalanine.

Kaempferol is believed to increase the effects of cannabinoids by reducing the number of molecules responsible for the breakdown of cannabinoids. Kaempferol has also been shown to have antinociceptive and anti-inflammatory activities. In certain embodiments, the kaempferol may be sourced from the leaves of *Tilia argentea*. A skilled artisan may select any suitable source of kaempferol, as desired.

Kaempferol may be provided in a powdered form. The powdered form may be commercially available from Pure Bulk, Inc., which is located in Roseburg, Oreg.

The kaempferol may be present in a concentration ranging from about 10 to about 50 weight percent, more particularly about 20 percent to about 40 percent, and most particularly about 33 percent. A skilled artisan may also select other suitable concentrations for the kaempferol component, as desired.

In particular, where the nutraceutical formulation is provided in a 17,400 mg daily dose, the kaempferol may be present in an amount of approximately 750 mg to 6,000 mg, more particularly approximately 2,250 mg to 4,500 mg, and most particularly about 5,700 mg. A skilled artisan may select any suitable amount of kaempferol for each particular daily dose of the nutraceutical formulation, as desired.

Probiotics have been found useful for unblocking receptors. In certain embodiments, the probiotics may include *Lactobacillus acidophilus* and *Streptococcus thermopholis*. *L. acidophilus* occurs naturally in the human body as well as many fermented foods, such as sauerkraut and miso. *S. thermophilus* is found in fermented milk products.

*Lactobacillus acidophilus* has been shown to modulate intestinal pain and induce cannabinoid receptors. *Streptococcus thermopholis* has been shown to enhance the effect of *Lactobacillus acidophilus*. In certain embodiments, the *Lactobacillus acidophilus* may be present in an amount of $1\times10^9$ CFU/g. A skilled artisan may select any suitable amount of *Lactobacillus acidophilus*, as desired.

In particular, where the nutraceutical formulation is provided in a 17,400 mg daily dose, the at least one probiotic may be present in an amount of $1.5\ 10^{10}$ CFU.

In certain embodiments, the nutraceutical formulation may also include whole coffee fruit. The whole coffee fruit may provide a source of caffeine in the formulation. Caffeine has been shown to suppress cannabinoids. A skilled artisan may also select a suitable amount of coffee fruit within the scope of the present disclosure.

In additional embodiments, the nutraceutical formulation may also optionally include chocolate. The chocolate may provide another source of caffeine in the formulation. Chocolate has also been shown to produce an effective amount of anandamide to mimic the effects of plant-derived cannabinoids.

Anandamide has been shown to interact with CB1 receptors. The chocolate may be present in an amount of 0 to 100 grams, more particularly approximately 25 grams to 75 grams, most particularly about 50 grams. A skilled artisan may also select a suitable amount of chocolate, as desired.

In other embodiments, the formulation may include green tea-EGCG and aromatic spices. The aromatic spices may include oregano and cinnamon, as non-limiting examples. Though not tied to any specific theory, these ingredients may aid the endocannabinoid system through antioxidant activities.

The aforementioned natural ingredients may be dried, ground, and mixed together by conventional techniques. Thereafter, the powder mixture may be pressed and formed into tablets, or placed in capsules, for oral administration.

It is further believed that the aforementioned ingredients, when used in combination in the concentrations described herein, may behave synergistically to unblock receptors in users to whom the nutraceutical formulation is administered on a consistent and regular basis.

The present disclosure is not only defined by the ingredients present in the nutraceutical formulation, but also by ingredients purposely omitted or avoided. It should be appreciated that these omitted ingredients may hinder the unblocking of receptors. One of ordinary skill in the art may also determine other such ingredients to be omitted, and particularly ingredients that may otherwise not contribute to unblocking receptors, within the scope of the present disclosure.

As may be presented herein, the language "consisting essentially of" is meant to limit the scope of the claim to the specified materials that do not materially affect the basic and novel characteristics of the nutraceutical formulation. Thus, the nutraceutical formulation consisting essentially of arachidonic acid, docosahexaenoic acid, *echinacea*, kaempferol, at least one probiotic, excludes ingredients which may materially affect the basic and novel characteristics of the nutraceutical formulation.

In particular applications, ingredients which materially affect the basic and novel characteristics of the nutraceutical formulation may include ingredients that affect the therapeutic effects or "high" of marijuana. More particularly, ingredients that have been shown to decrease the efficacy of marijuana are omitted from the nutraceutical formulation as the nutraceutical formulation is configured to allow a patient to more easily reach the therapeutic dose of marijuana.

While bound to no particular theory, it is believed that foods high in terpenes may materially affect a patient's reaction to cannabinoids. For example, black pepper, pine nuts, mangoes, and lemons have high levels of terpenes. The terpenes present in these foods may interact with the terpenes found in marijuana in such a way that it materially affects the ability of the patient to receive the therapeutic dose.

It should be appreciated that, where the aforementioned ingredients of the formulations are sourced from whole foods, the whole foods themselves will not be used as the ingredients if they are believed to have an undesirably high concentration of terpenes, for these reasons.

Additionally, as may be presented in the claims below, the language "consisting of" is intended to exclude any ingredient not specified in the claim. Accordingly, the nutraceutical formulation consisting of arachidonic acid, docosahexaenoic acid, echinacea, kaempferol, at least one probiotic includes only those ingredients.

EXAMPLE

In one example, the nutraceutical formulation, including arachidonic acid, docosahexaenoic acid, echinacea, kaempferol, at least one probiotic is administered to patients in a daily oral dose. In particular, the dosage amounts of arachidonic acid, docosahexaenoic acid, echinacea, kaempferol, *Lactobacillus acidophilus* are shown below in TABLE 1.

TABLE 1

Dosage of Nutraceutical Formulation

| Ingredients | Weight |
|---|---|
| Arachidonic acid | 8,000 mg |
| Docosahexaenoic acid | 3,300 mg |
| *Echinacea* | 400 mg |
| Kaempferol | 5,700 mg |
| *Lactobacillus acidophilus* | $1.74 \times 10^{10}$ CFU |

The nutraceutical formulation, as shown in TABLE 1 above, will be administered daily to a patient. If the patient would have an established tolerance to cannabinoids, the nutraceutical formulation would be expected to minimize the established tolerance. If the patient would not have the established tolerance for cannabinoids, the nutraceutical formulation would be expected to militate against the formation of tolerance for cannabinoids.

It should be appreciated that a tolerance to cannabinoids may result in a need for an increased dosage of cannabinoids in order to receive a therapeutic dose. Accordingly, the patient with an established tolerance for cannabinoids would require a larger dose of cannabinoids, compared to the patient with no established tolerance to reach similar therapeutic effects from the dose of cannabinoid for each patient.

For example, the effects of the nutraceutical formulation may be shown comparatively between two patients, each exhibiting the established tolerance to cannabinoids. By way of example, each of the two patients would require 100 mg of cannabinoid to reach the desired therapeutic dose. A first patient would ingest the daily dose of the nutraceutical formulation shown in TABLE 1 for a week, and a second patient would be given a daily dose of a placebo for a week. After the weekly dosing regimen, the first patient would be expected to require less than 100 mg of cannabinoid to receive the therapeutic dose, where the second patient would be expected to still require 100 mg to receive the therapeutic dose.

Additionally, it has been shown that the half-life of certain cannabinoids in a patient with the established tolerance is less than the half-life of the certain cannabinoids in the patient without the established tolerance. Accordingly, following the week of oral administration of the nutraceutical formulation to the first patient, and the placebo to the second patient, a blood test would be performed. The blood test may be expected to show that the half-life of the cannabinoids in the blood of the first patient is greater than the half-life of the cannabinoids in the blood of the second patient.

It should be understood that this disclosure contemplates the unblocking of any suitable receptors. However, as a non-limiting example, the nutraceutical formulation may be particularly suited for unblocking cannabinoid receptors in the endocannabinoid system.

Accordingly, the nutraceutical formulation may militate against the formation of a tolerance to cannabinoids in a patient who uses medical marijuana. Desirably, the nutraceutical formulation may unsaturated the CB1 and CB2 receptors, which may allow the cannabinoids to more easily bind to such receptors. Thus, the patient will require less cannabinoids to reach a therapeutic dose.

While certain representative embodiments and details have been shown for purposes of illustrating the invention, it will be apparent to those skilled in the art that various changes may be made without departing from the scope of the disclosure, which is further described in the following appended claims.

What is claimed is:

1. A nutraceutical formulation for facilitating unblocking cannabinoid receptors, consisting essentially of:
    arachidonic acid;
    docosahexaenoic acid;
    *echinacea;*
    kaempferol; and
    a probiotic,
    wherein the nutraceutical formulation is in a unit dosage form of a tablet or capsule.

2. A nutraceutical formulation for facilitating unblocking cannabinoid receptors, consisting of:
    arachidonic acid;
    docosahexaenoic acid;
    *echinacea;*
    kaempferol; and
    a probiotic,
    wherein the nutraceutical formulation is in a unit dosage form of a tablet or capsule.

* * * * *